United States Patent [19]
Ariki et al.

[11] Patent Number: 4,507,514
[45] Date of Patent: * Mar. 26, 1985

[54] METHOD FOR PURIFYING 1,2-DICHLOROETHANE

[75] Inventors: Yusaku Ariki; Takio Hino; Noboru Yoshida, all of Takasago, Japan

[73] Assignee: Kanegafuchi Kagaku Kogyo Kabushiki Kaisha, Osaka, Japan

[*] Notice: The portion of the term of this patent subsequent to Sep. 28, 1999 has been disclaimed.

[21] Appl. No.: 425,696

[22] Filed: Sep. 28, 1982

Related U.S. Application Data

[63] Continuation-in-part of Ser. No. 246,154, Mar. 23, 1981, Pat. No. 4,351,976.

[30] Foreign Application Priority Data

Mar. 26, 1980 [JP] Japan .................................. 55-39591

[51] Int. Cl.$^3$ ............................................... B01D 3/34
[52] U.S. Cl. ..................................... 570/262; 203/51; 203/67
[58] Field of Search ............... 570/262, 243, 246, 252; 203/50, 57, 67, 71, 68, 70, 51

[56] References Cited

PUBLICATIONS

"Vinyl Chloride", in Hydrocarbon Processing, Nov. 1975, at p. 216.

Primary Examiner—Frank Sever
Attorney, Agent, or Firm—Armstrong, Nikaido, Marmelstein & Kubovcik

[57] ABSTRACT

An improvement of a method for purifying 1,2-dichloroethane by passing through a distillation column a crude 1,2-dichloroethane produced by oxychlorination of ethylene with at least one of a crude 1,2-dichloroethane produced by direct chlorination of ethylene and a crude uncracked 1,2-dichloroethane recovered in thermal cracking of 1,2-dichloroethane, the improvement which comprises feeding the oxychlorination-produced 1,2-dichloroethane to an upper plate of the distillation column which is above a plate of the column to which at least one of the direct chlorination-produced 1,2-dichloroethane and the uncracked 1,2-dichloroethane is fed, and recovering 1,2-dichloroethane as a bottom product. The purification method is very useful in the production of vinyl chloride by thermal cracking of 1,2-dichloroethane since carbon tetrachloride effective as a thermal cracking catalyst is recovered in concentrations stabilized within the range of ±500 p.p.m. with 1,2-dichloroethane, while removing other low boiling impurities, and since the method is economically practiced.

8 Claims, 4 Drawing Figures

METHOD FOR PURIFYING 1,2-DICHLOROETHANE

CROSS-REFERENCE TO RELATED APPLICATIONS

This is a continuation-in-part of application Ser. No. 246,154 filed on Mar. 23, 1981, now U.S. Pat. No. 4,351,976.

BACKGROUND OF THE INVENTION

The present invention relates to the purification of 1,2-dichloroethane (ethylene dichloride), and more particularly to an improvement of a method for purifying crude 1,2-dichloroethane by employing a distillation column of plate type or packed type.

At the present day, vinyl chloride has been in general prepared industrially by a process in which purified 1,2-dichloroethane is thermally cracked. Crude 1,2-dichloroethane produced by oxychlorination of ethylene (hereinafter referred to as "oxy-EDC"), crude 1,2-dichloroethane produced by direct chlorination of ethylene (hereinafter referred to as "direct-EDC") and uncracked 1,2-dichloroethane (hereinafter referred to as "uncracked-EDC") recovered in the thermal cracking of 1,2-dichloroethane are purified and employed as a feed 1,2-dichloroethane in the production of vinyl chloride monomer (hereinafter referred to as "VCM") by an oxychlorination process.

The crude oxy-EDC usually contains as impurities low-boiling compounds (having a boiling point of not more than 83.7° C./760 mmHg) such as ethyl chloride, cis-dichloroethylene, chloral, carbon tetrachloride and trichloroethylene and high-boiling compounds (having a boiling point of not less than 83.7° C./760 mmHg) such as 1,1,2-trichloroethane and tetrachloroethane. On the other hand, the crude direct-EDC usually contains as impurities low-boiling compounds such as ethyl chloride, 1,1-dichloroethane and chloroform and high-boiling compounds such as 1,1,2-trichloroethane and tetrachloroethane. Also, the uncracked-EDC usually contains as impurities low-boiling compounds such as ethyl chloride, chloroprene and chloroform and high-boiling compounds such as monochlorobenzene.

A distillation column has been employed for purifying these crude 1,2-dichloroethanes of three kinds to the extent such that 1,2-dichloroethane (hereinafter referred to as "EDC") can be cracked without any problems to produce VDC of usual quality. FIG. 1 is a flow sheet showing a conventional purification method using a distillation column. In general, the purification is carried out by passing the crude EDC first through a so-called low boiler column I for removing impurities having lower boiling points than EDC and then through a high boiler column II for removing impurities having higher boiling points than EDC. In a conventional purification method, in order to remove the low-boiling compounds, the above-mentioned crude EDC of three kinds are usually mixed at an appropriate place in an appropriate manner and are fed through a feed pipe 1 to a certain appropriate one plate of the low boiler column I, and low-boiling compounds are distilled from the top of the column through a pipe 3. The bottom product is then fed through a pipe 4 to the high boiler column II, and the purified EDC is recovered from the top of the column through a pipe 5, while high-boiling impurities are removed from the bottom of the column through a pipe 6. In the low boiler column I, it is necessary to purify the crude EDC so that EDC recovered as a bottom product from the bottom of the column contains no low-boiling compounds, or even if contians, the amount of low-boiling compounds is so small that they do not hinder the thermal cracking of EDC in the production of vinyl chloride, in other words, do not decrease the thermal cracking rate and also do not cause clogging of a reaction tube, e.g. less than several hundreds p.p.m. When carbon tetrachloride included in the crude oxy-EDC, which is effective as a catalyst for thermal cracking of EDC, is recovered as a bottom product together with EDC, it is possible to conduct the thermal cracking of EDC at a relatively low temperature, since the purified EDC contains the carbon tetrachloride catalyst.

However, in a conventional distillation method as mentioned above in which the mixed crude EDC is fed to a certain one plate of a distillation column, the attempt of including carbon tetrachloride into the purified EDC without increasing the feed amount of steam has accompanied the defect that the concentration of other low-boiling compounds in the purified EDC also increases. On the other hand, when it is attempted to decrease the concentration of low-boiling compounds, carbon tetrachloride is also distilled away together with other low-boiling compounds. Further, when the amount of supplied steam is increased in order to raise the concentration of carbon tetrachloride in the purified EDC with keeping the concentration of other low-boiling compounds low, not only the utility cost increases, but also the concentration of carbon tetrachloride largely changes by a slight change in the conditions of operating a low boiler column, so upon preparing VCM by thermal cracking of the thus purified EDC, the conversion is not stabilized.

Accordingly, it is an object of the present invention to provide an improved method for purifying the crude oxy-EDC, crude direct-EDC and uncracked-EDC by employing a distillation column, which has a great effect in steam saving.

A further object of the invention is to provide an improved method of purifying crude EDC by which, in one distillation column for removing low-boiling impurities, the fluctuation range of the intended concentration of carbon tetrachloride contained in a bottom product can be controlled within the range of ±500 p.p.m. over a wide range of the concentration of carbon tetrachloride, practically 0 to 8,000 p.p.m., so that the conversion of the purified EDC into vinyl chloride by thermal cracking is stabilized.

Another object of the present invention is to provide a method for producing VCM having a stable quality with a decreased amount of energy from a crude EDC by subjecting the purified EDC, obtained by the above purification method, having a stabilized concentration of carbon tetrachloride, to thermal cracking at a high and stable rate of thermal cracking.

These and other objects of the present invention will become apparent from the description hereinafter.

SUMMARY OF THE INVENTION

In accordance with the present invention, there is provided an improvement of a method for purifying 1,2-dichloroethane by passing through a distillation column a crude 1,2-dichloroethane produced by oxychlorination of ethylene with at least one of a crude 1,2-dichloroethane produced by direct chlorination of ethylene and a crude uncracked 1,2-dichloroethane recovered in thermal cracking of 1,2-dichloroethane, the improvement which comprises feeding a crude 1,2-dichloroethane produced by the oxychlorination to an upper plate of a distillation column, feeding to at least one plate sufficiently below said upper plate at least one crude 1,2-dichloroethane of a crude 1,2-dichloroethane produced by the direct chlorination and a crude uncracked 1,2-dichloroethane recovered in thermal cracking, and recovering 1,2-dichloroethane as a bottom product containing 0 to 8,000 p.p.m. of carbon tetrachloride, the concentration of said carbon tetrachloride being stabilized within the fluctuation range of ±500 p.p.m.

The purification can be conducted with a less amount of steam and the distillation purification capacity can be improved. The purified EDC is subjected to thermal cracking to produce VCM after passing through a high boiler column to remove high-boiling impurities. Since the purified EDC contains a stabilized concentration of carbon tetrachloride, it is possible to stably conduct the thermal cracking. Also, the purified EDC containing a catalytically effective amount of carbon tetrachloride in a stabilized concentration provides VDC in stable, high conversions by the thermal cracking at a relatively low temperature. Thus, VCM of a stable quality can be prepared with a decreased fuel consumption in an improved productive capacity. The present invention also provide a method for producing VCM which can be practiced under industrially advantageous conditions.

DETAILED DESCRIPTION

According to the method of the present invention in which at least two kinds of crude EDC are fed to two or three appropriate plates of a low boiler column, low-boiling compounds can be removed as a distillate with a far less amount of steam than that required in a conventional method in which crude EDCs are fed to one plate of a low boiler column. It is possible to decrease the amount of steam supplied to the distillation column to about ⅓ time that required in a conventional method. Also, carbon tetrachloride which is useful as a catalyst in thermal cracking of EDC for the production of VCM, can be accumulated into the purified EDC subjected to the cracking reaction more easily in a stable concentration and economically as compared with a conventional feeding method, since carbon tetrachloride included in feed materials can be recovered with EDC as a bottom product, and since in a preferable embodiment, after thermal cracking of EDC carbon tetrachloride is recycled with the uncracked EDC. According to the method of the present invention, it is possible not only to control the concentration of carbon tetrachloride over a wide range from 0 to 8,000 p.p.m., but also to keep the fluctuation of the intended concentration of carbon tetrachloride within the range of ±500 p.p.m., while the concentration of low boiling compounds to be removed can be kept low. Preferably, the concentration of carbon tetrachloride in the EDC recovered as a bottom product is maintained at 1,000 to 5,000 p.p.m., especially 3,000 to 5,000 p.p.m. Further, when VCM is prepared by subjecting EDC purified according to the method of the invention which contains carbon tetrachloride in a stable concentration, to thermal cracking, the average conversion of EDC into VCM is stabilized on a high level as compared with the use of EDC purified by a conventional method containing a noticeably fluctuating concentration of carbon tetrachloride, and accordingly it is possible to conduct the operation of thermal cracking under industrially advantageous conditions.

In the present invention, a known column such as a plate column or a packed column can be employed as a distillation column.

Figure 1:
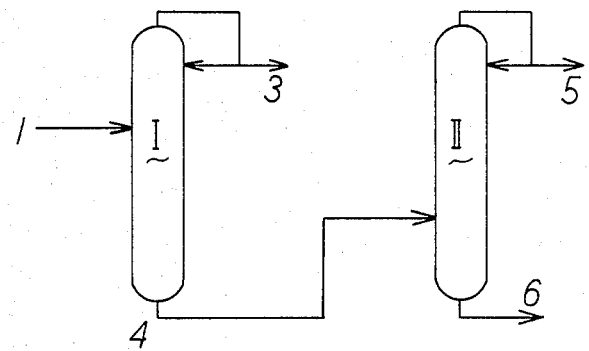
FIG. 1 is a flow sheet illustrating a conventional distillation system by one plate EDC feeding.
Figure 2:
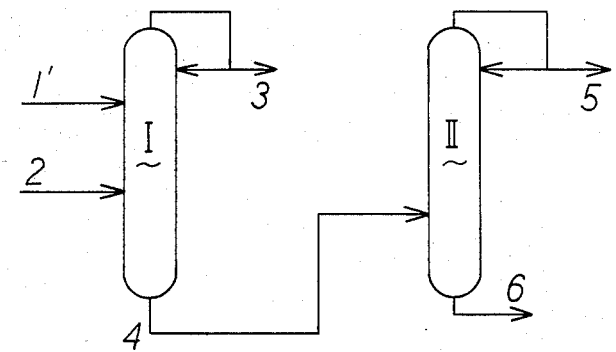
FIG. 2 is a flow sheet illustrating a distillation system according to the present invention by multi-plate EDC feeding.

An embodiment of the purification method of the present invention is explained in detail below with reference to FIG. 2.

A crude oxy-EDC containing carbon tetrachloride is fed through a pipe 1' to a plate positioned slightly lower than the top of a distillation column I for removal of low-boiling compounds, and simultaneously at least one of direct-EDC and an uncracked-EDC is fed through a pipe 2 to a lower plate of the column I than the oxy-EDC feed plate. It is preferable to employ with the direct-EDC as a feed material the uncracked-EDC recovered in the production of VCM by thermal cracking of EDC, since the concentration of carbon tetrachloride in the obtained purified EDC can be readily increased to a desired concentration, though the energy saving effect can be obtained even if the uncracked-EDC is not recycled.

In the early stage of the operation, even if a large portion of carbon tetrachloride included in the oxy-EDC is recovered in the purified EDC, its concentration is relatively low, since the uncracked-EDC contains scarcely carbon tetrachloride. However, since carbon tetrachloride made once to include in the purified EDC remains almost in the uncracked-EDC in the thermal cracking step of EDC for the production of VCM and is fed again to the low boiler column I in a circulating manner, the concentration of carbon tetrachloride in the obtained purified EDC is gradually increased. Therefore, it is possible to increase the concentration of carbon tetrachloride to a desired concentration without adding carbon tetrachloride from the outside. The concentration of carbon tetrachloride in the uncracked-EDC at that time is higher than that in the oxy-EDC. Thus, upon recovering carbon tetrachloride, it is efficient to make the recovery percentage from the uncracked-EDC containing a relatively high concentration of carbon tetrachloride higher than the recovery percentage from the oxy-EDC containing a relatively low concentration of carbon tetrachloride. This is also important in stabilizing the concentration of carbon tetrachloride. Also, it is a key point for efficiently removing low-boiling compounds to make the removal percentage of low-boiling compounds from the oxy-EDC containing them in high concentrations higher than the removal percentage of low-boiling compounds from the uncracked-EDC and direct-EDC containing them in low concentrations.

The recovery percentage of carbon tetrachloride and the removal percentage of low-boiling compounds are determined by the ratio of the amount of a falling liquid to the amount of a rising gas within the column. According to the method of the present invention, it is possible to raise the ratio of gas to liquid and thus to raise the removal percentage of low-boiling compounds by feeding the oxy-EDC to an upper plate of the column, and it is possible to lower the ratio of gas to liquid and thus to raise the recovery percentage of carbon tetrachloride by feeding the direct-EDC and/or the uncracked-EDC to a lower plate of the column. In order to effectively practice the present invention, it is desirable that the number of the plates between the upper plate to be fed with the oxy-EDC and the lower plates to be fed with the direct-EDC and/or the uncracked-EDC, the number of the plates between the top of the column and the upper plate and the number of the plates between the lower plate and the bottom of the column are at least 10 plates, respectively, but are not critical.

Also, in order to effectively practice the present invention, it is desirable to feed the whole amount of the oxy-EDC, the whole amount of the uncracked-EDC and the whole amount of the direct-EDC which are produced or recovered in a VCM manufacturing plant by an oxychlorination process, to the upper portion, the middle portion and the lower portion of the distillation column, respectively. However, in the practical operation, it is not necessary to define the column into three portions and to completely separately feed the crude EDC of three kinds. The saving of steam, the inclusion of carbon tetrachloride into the purified EDC and the stabilization of the concentration of carbon tetrachloride can be easily attained by feeding the crude oxy-EDC to an upper plate of distillation column which is above a plate of the column to which other crude EDC, i.e. at least one of the direct-EDC and the uncracked-EDC, is fed. The crude oxy-EDC to be fed to the upper plate of the column may be the oxy-EDC alone or a mixture of a major amount of oxy-EDC and a minor amount of other crude EDC, i.e. direct-EDC and/or uncracked-EDC. The crude EDC to be fed to the lower plate than the upper oxy-EDC feed plate may be the direct-EDC alone, the uncracked-EDC alone, a mixture of the direct-EDC and the uncracked-EDC or a mixture of a major amount of at least one of the direct-EDC and the uncracked-EDC and a minor amount of the oxy-EDC. In case of feeding a mixed crude EDC, the ratio of the oxy-EDC contained in the total EDC fed to the upper plate always has to be higher than the ratio of the oxy-EDC contained in the total EDC fed to the lower plate.

In a VCM manufacturing plant according to a usual balanced process, the proportion of the oxy-EDC, uncracked-EDC and direct-EDC is about 1:2:1 when the conversion of the purified EDC is kept 50%.

When the method of the present invention is most efficiently practiced, the amount of steam supplied to the low boiler column can be reduced to about ⅓ time that required in a conventional method. In addition to such a large energy saving, it is also possible to suitably control the concentration of carbon tetrachloride in the purified EDC obtained through a high boiler column within the range of 0 to 8,000 p.p.m. The more important feature of the present invention is that the concentration of carbon tetrachloride can be stabilized within the range of ±500 p.p.m. at every desired concentration of carbon tetrachloride within the range of 0 to 8,000 p.p.m. This feature is very advantageous for the production of VCM, particularly in the case where carbon tetrachloride is recovered in high concentrations with EDC as a bottom product. That is to say, when the purified EDC containing a stable concentration of carbon tetrachloride useful as a thermal cracking catalyst is subjected to thermal cracking, the rate of thermal cracking of EDC, namely the conversion of EDC into VCM, is stabilized, and consequently the average conversion of EDC can be stably mintained on a high level. Also, since a high average conversion can be attained, the amount of the uncracked-EDC to be recycled is decreased, whereby the amount of steam required in purification is decreased, and also consumption of fuel in thermal cracking is decreased. As a result, the total capacity of a VCM manufacturing plant, including the capacity of the distillation column for purifying EDC and the capacity of the cracking furnace for producing VCM, can be improved by such effects combined with the effects obtained by the specific multiplate feeding of crude EDC to a distillation column.

There is the following relationship between the rate of thermal cracking kp and the conversion x in the thermal cracking reaction of EDC under a constant pressure and a constant amount of EDC fed, and they depend on the thermal cracking temperature and concentration of carbon tetrachloride.

$$kp = \frac{F}{V \cdot P} [-x - 2\ln(1-x)] = [CCl_4]A \cdot e^{-E/RT}$$

wherein kp is a rate constant of reaction, F is a rate of feeding a raw material (EDC), V is a volume of a reactor, P is an operation pressure, x is a conversion, $[CCl_4]$ is a concentration of carbon tetrachloride, A is a frequency factor, T is a temperature and E is an activation energy.

Figure 3A:
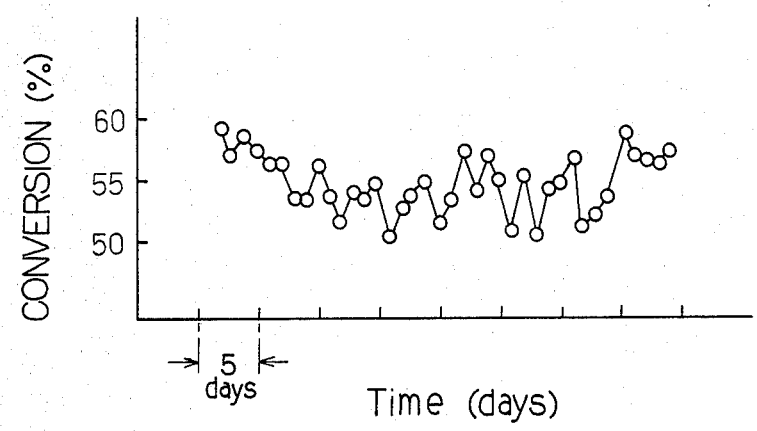
FIGS. 3A and 3B are graphs showing fluctuation ranges of conversion of EDC in thermal cracking of EDC purified by a conventional method and EDC purified by the method of the present invention.
Figure 3B:
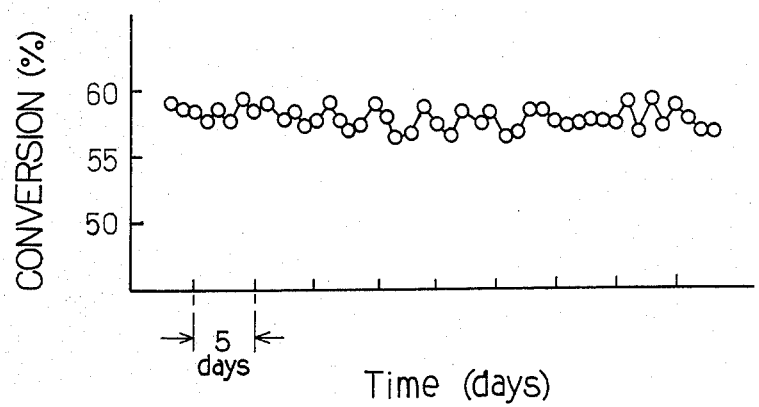

Improvement of the conversion by raising the reaction temperature is subject to restriction in the strength of the reactor material, increase of coking and increase of concentration of impurities in VCM. The presence of carbon tetrachloride is effective, since the conversion can be increased within the temperature range which does not exert such bad influences. For the reason, in a conventional VCM manufacturing plant carbon tetrachloride has been added to purified EDC from the outside. In a conventional method for purifying EDC, it is possible to recover carbon tetrachloride with EDC as a bottom product by supplying an increased large amount of steam, but is very difficult to stabilize the concentration of carbon tetrachloride included in the purified EDC. When such an EDC is subjected to the thermal cracking, VCM cannot be produced under stable conditions, since the concentration of carbon tetrachloride largely fluctuates all the time. The fluctuation range of the carbon tetrachloride concentration can be stably controlled within the range of ±500 p.p.m. with the reduction effect of the consumption of steam by feeding crude EDC to a low boiler column in a multi-plate feeding manner according to the present invention. FIGS. 3A and 3B are graphs showing fluctuation ranges of the conversion of EDC in thermal cracking of EDC purified by a conventional method and EDC purified by the method of the present invention. FIG. 3B shows the conversion of EDC purified according to the method of the invention and containing 3,200 to 3,800 p.p.m. of carbon tetrachloride (average concentration: 3,500 p.p.m.). The conversion of EDC is from 56.5 to 59.5% and is 58% on an average. FIG. 3A shows the conversion of EDC purified according to a conventional method in which carbon tetrachloride is accumulated only in a concentration of 1,000 p.p.m. on an average, and the concentration fluctuates between 300 p.p.m. and 2,000 p.p.m. The conversion of EDC fluctuates between 51% and 59% in accordance with the fluctuation of the carbon tetrachloride concentration and is 55% on an average. In FIGS. 3A and 3B, the conversion of EDC purified according to the method of the invention is higher by 3% on an average than that of EDC purified according to a conventional method.

The effect for stabilizing the carbon tetrachloride concentration can be attained substantially at almost all the desired concentration. That is to say, the concentration of carbon tetrachloride can be stabilized within the range of ±500 p.p.m. with respect to the desired carbon tetrachloride concentration over low concentrations below 500 p.p.m. to high concentrations such as 8,000 p.p.m. According to the method of the present invention, it is possible to easily maintain carbon tetrachloride to be included in the purified EDC at a desired concentration, and even in the case where the target carbon tetrachloride concentration is low, the fluctuation range thereof is narrow. For instance, in case that the target average concentration of carbon tetrachloride is not more than 300 p.p.m., the fluctuation of the concentration is from 0 to 500 p.p.m., whereas according to a conventional method the concentration fluctuates between 0 and 1,000 p.p.m. The catalytic action of carbon tetrachloride in thermal cracking of EDC is observed from several p.p.m. and increases with increasing concentrations of carbon tetrachloride. The catalytic effect is nearly on the same level over 4,000 p.p.m. Therefore, in the case of concentrating carbon tetrachloride into the purified EDC, the purification is usually operated so that the concentration of carbon tetrachloride falls within the range of 1,000 to 5,000 p.p.m., preferably 3,000 to 5,000 p.p.m., under a steady operation. The concentration can be easily changed to a desired one, if necessary, and moreover the fluctuation thereof can be maintained small. Therefore, these features of the invention are very advantageous for practical plant operation.

The control of the carbon tetrachloride concentration can be conducted by adjustment of the concentration of low-boiling compounds in the liquid at the top of the low boiler column. The temperature of a suitable specific plate at the concentrating portion of the column is usually used as a substitution characteristic for this purpose. Thus, by controlling the temperature of the concentrating portion of the column, carbon tetrachloride can be easily recovered with purified EDC as a bottom product in a desired concentration, while removing other compounds having a lower boiling point than that of carbon tetrachloride as a distillate from the top of the column.

Also, according to the present invention, it is possible to decrease the sectional area of a distillation column and the heat transfer areas of a cooler and a reboiler to ⅓ time those in a conventional method and, therefore, the construction cost can be cut down. The economical efficiency of the present invention is scarcely influenced by the construction cost of EDC feeding equipment newly installed for practicing the present invention. Thus, the present invention not only provides an economical method for the purification of EDC, but also has the advantages of the reduction of the construction cost, easiness of the operation and easiness of the industrialization.

The method of the present invention is more specifically described and explained by means of the following Examples and Comparative Examples, in which all % and p.p.m. are by mole unless otherwise noted. It is to be understood that the present invention is not limited to the Examples and various changes and modifications may be made in the invention without departing from the spirit and scope thereof.

COMPARATIVE EXAMPLE 1

To the 60th plate from the bottom of a low boiler distillation column consisting of 75 plates were fed 15 tons/hour of a crude oxy-EDC of 96.3% in purity containing 840 p.p.m. of carbon tetrachloride obtained by oxychlorination of ethylene, 15 tons/hour of a crude direct-EDC of 99.5% in purity containing 30 p.p.m. of carbon tetrachloride obtained by direct chlorination of ethylene and 30 tons/hour of uncracked-EDC of 99.8% in purity containing 750 p.p.m. of carbon tetrachloride. The amount of a liquid taken out from the top of the column was adjusted so that the temperature of the 70th plate was maintained at 120° C., and steam was supplied to a reboiler located at the bottom of the column in an amount of 12.8 tons/hour. The concentration of the purified EDC recovered from the column bottom fluctuated between 90 p.p.m. and 850 p.p.m. The purified EDC contained 350 p.p.m. of carbon tetrachloride on an average and 170 p.p.m. in total of other low-boiling compounds.

In order to increase the concentration of carbon tetrachloride, the steam supplied to the reboiler was increased to 15.5 tons/hour and the temperature of the 70th plate was lowered by 8° C. The purified EDC obtained from the column bottom after 6 hours from the above operation contained 3,000 p.p.m. of carbon tetrachloride, but the concentration of carbon tetrachloride was not stabilized and varied within the range of 1,600 to 4,100 p.p.m. The maximum concentration of other low-boiling compounds in the purified EDC during this operation was 200 p.p.m.

EXAMPLE 1

According to the method of the present invention, 15 tons/hour of a crude oxy-EDC of 96.3% in purity containing 840 p.p.m. of carbon tetrachloride was fed to the 60th plate from the bottom of a low boiler distillation column consisting of 75 plates, and 15 tons/hour of a crude direct-EDC of 99.5% in purity containing 30 p.p.m. of carbon tetrachloride and 30 tons/hour of uncracked-EDC of 99.8% in purity containing 750 p.p.m. of carbon tetrachloride were fed to the 30th plate from the bottom of the column. Steam was supplied to a reboiler in an amount of 4 tons/hour, and the temperature of the 70th plate was adjusted to 112° C. The concentration of carbon tetrachloride in the purified EDC obtained from the column bottom was 3,200 p.p.m. after 6 hours from the starting of the operation and increased to 3,700 p.p.m. after 3 days, but thereafter did not increase.

After 3 days from starting the operation, the temperature of the 70th plate was lowered by 2° C., and the operation was continued. The concentration of carbon tetrachloride was 6,400 p.p.m. after 6 hours, and increased to 7,800 p.p.m. after 3 days. Thereafter, the concentration of carbon tetrachloride fluctuated between 7,000 p.p.m. and 7,800 p.p.m. and was 7,500 p.p.m. on an average. The maximum concentration of other low-boiling compounds during this operation was 150 p.p.m. and the change in its concentration was slight.

EXAMPLE 2

By employing the same crude EDC and distillation column as those employed in Example 1, 22.5 tons/hour of a mixed EDC containing the oxy-EDC, the direct-EDC and the uncracked-EDC in a molar ratio of 12.5:5:5 was fed to the 60th plate from the bottom of the column, and 37.5 tons/hour of a mixed EDC containing the oxy-EDC, the direct-EDC and the uncracked-EDC in a molar ratio of 2.5:10:25 was fed to the 30th plate from the bottom of the column. Steam was supplied to the reboiler in an amount of 6.5 tons/hour. The concentration of carbon tetrachloride in the purified EDC obtained from the column bottom fluctuated between 3,050 p.p.m. and 3,500 p.p.m., and was 3,300 p.p.m. on an average. The maximum concentration of other low-boiling compounds in the purified EDC during this operation was 200 p.p.m. and the change in its concentration was slight.

EXAMPLE 3

The purification of the crude EDC was carried out in the same manner as in Example 1 except that 15 tons/hour of the oxy-EDC was fed to the 60th plate, 15 tons/hour of the direct-EDC and 30 tons/hour of the uncracked-EDC were fed to the 30th plate, 3.5 tons/hour of steam was supplied to the reboiler, and the temperature of the 70th plate was adjusted to 117° C. The concentration of carbon tetrachloride in the purified EDC obtained from the column bottom was 60 p.p.m. after 6 hours and increased to 340 p.p.m. after 3 days, but thereafter it did not increase. The concentration of other low-boiling compounds was about 130 p.p.m. during this operation and the change in its concentration was slight.

In order to increase the concentration of carbon tetrachloride, the temperature of the 70th plate of the low boiler column was lowered to 114° C. and the purification was continued. The concentrations of carbon tetrachloride and other low-boiling compounds were 4,800 p.p.m. and 260 p.p.m. after 6 hours, respectively. After 3 days, the concentrations of carbon tetrachloride and the low-boiling compounds increased to 6,200 p.p.m. and 290 p.p.m. respectively, but thereafter they did not increase. The concentration of carbon tetrachloride fluctuated between 5,900 p.p.m. and 6,200 p.p.m.

COMPARATIVE EXAMPLE 2

The purification of the crude EDC was carried out in the same manner as in Example 1 except that the uncracked-EDC was fed to the 60th plate, the oxy-EDC and direct-EDC were fed to the 30th plate, 15.5 tons/hour of steam was supplied to the reboiler and the temperature of the 70th plate was adjusted to 112° C. The concentration of carbon tetrachloride in the purified EDC obtained from the column bottom varied between 550 p.p.m. and 2,700 p.p.m. and was 1,800 p.p.m. on an average. Also, the concentration of other low-boiling compounds was 230 p.p.m.

COMPARATIVE EXAMPLE 3

The procedure of Comparative Example 2 was repeated except that steam was supplied to the reboiler in an amount of 4 tons/hour. The concentration of carbon tetrachloride in the purified EDC obtained from the bottom product fluctuated between 2,400 p.p.m. and 5,700 p.p.m., and was 4,600 p.p.m. on an average. Also, the concentration of other low-boiling compounds was 8,700 p.p.m.

COMPARATIVE EXAMPLE 4

The procedure of Comparative Example 2 was repeated except that the temperature of the 70th plate was maintained at 117° C. The concentration of carbon tetrachloride fluctuated between 70 p.p.m. and 800 p.p.m. The maximum concentration of other low-boiling compounds was 180 p.p.m.

The results obtained in Examples 1 to 3 and Comparative Examples 1 to 4 are shown in the following Table.

|  | Example 1 | | Example 2 | | Example 3 | |
| --- | --- | --- | --- | --- | --- | --- |
|  | Upper | Lower | Upper | Lower | Upper | Lower |
| Crude EDC fed (ton/hr.) | | | | | | |
| Oxy-EDC | 15 | — | 12.5 | 2.5 | 15 | — |
| Direct-EDC | — | 15 | 5 | 10 | — | 15 |
| Uncracked-EDC | — | 30 | 5 | 25 | — | 30 |
| Feed plate | | | | | | |
| Upper plate | 60th | | 60th | | 60th | |
| Lower plate | 30th | | 30th | | 30th | |
| Temp. of 70th plate (°C.) | 112 | 110 | 112 | | 117 | 114 |
| Steam (ton/hr.) | 4 | 4 | 6.5 | | 3.5 | 3.5 |
| Concentration of $CCl_4$ (p.p.m.) | 3200 to 3700 (ave. 3500) | 7000 to 7800 (ave. 7500) | 3050 to 3500 (ave. 3300) | | 60 to 340 | 5900 to 6200 |
| Quality of EDC | | | | | | |
| Concentration of low-boiling compounds (p.p.m.) | 150 | 150 | 200 | | 130 | 260 to 290 |

|  | Com. Ex. 1 | | Com. Ex. 2 | | Com. Ex. 3 | | Com. Ex. 4 | |
| --- | --- | --- | --- | --- | --- | --- | --- | --- |
|  | Upper | Lower | Upper | Lower | Upper | Lower | Upper | Lower |
| Crude EDC fed (ton/hr.) | | | | | | | | |
| Oxy-EDC | 15 | — | — | 15 | — | 15 | — | 15 |
| Direct-EDC | 15 | — | — | 15 | — | 15 | — | 15 |
| Uncracked-EDC | 30 | — | 30 | — | 30 | — | 30 | — |
| Feed plate | | | | | | | | |
| Upper plate | 60th | | 60th | | 60th | | 60th | |
| Lower plate | — | | 30th | | 30th | | 30th | |
| Temp. of 70th plate (°C.) | 120 | 112 | 112 | | 112 | | 117 | |
| Steam (ton/hr.) | 12.8 | 15.5 | 15.5 | | 4 | | 15.5 | |

| -continued | | | | | |
|---|---|---|---|---|---|
| Concentration of CCl₄ (p.p.m.) | 90 to 850 (ave. 350) | 1600 to 4100 (ave. 3000) | 550 to 2700 (ave. 1800) | 2400 to 5700 ave. 4600) | 70 to 800 (ave. 280) |
| Quality of EDC Concentration of low-boiling compounds (p.p.m.) | 170 | 200 | 230 | 8700 | 180 |

What we claim is:

1. In a method for purifying 1,2-dichloroethane by passing through a distillation column a crude 1,2-dichloroethane produced by oxychlorination of ethylene with at least one of a crude 1,2-dichloroethane produced by direct chlorination of ethylene and a crude uncracked 1,2-dichloroethane recovered in thermal cracking of 1,2-dichloroethane, the improvement which comprises feeding a crude 1,2-dichloroethane produced by the oxychlorination to an upper plate of a distillation column, feeding to at least one plate sufficiently below said upper plate at least one crude 1,2-dichloroethane of a crude 1,2-dichloroethane produced by the direct chlorination and a crude uncracked 1,2-dichloroethane recovered in thermal cracking, and recovering 1,2-dichloroethane as a bottom product containing 0 to 8,000 p.p.m. of carbon tetrachloride, the concentration of said carbon tetrachloride being stabilized within the fluctuation range of ±500 p.p.m.

2. The method of claim 1, wherein the crude 1,2-dichloroethane fed to the upper palte further contains as a minor component at least one of a crude 1,2-dichloroethane produced by the direct chlorination and a crude uncracked 1,2-dichloroethane recovered in the thermal cracking.

3. The method of claim 1, wherein said at least one crude 1,2-dichloroethane further contains as a minor component a crude 1,2-dichloroethane produced by the oxychlorination.

4. The method of claim 1, wherein carbon tetrachloride included in the crude 1,2-dichloroethane fed is recovered in a concentration of 1,000 to 5,000 p.p.m. together with 1,2-dichloroethane as a bottom product, while other compounds having a lower boiling point than carbon tetrachloride are removed as a distillate.

5. The method of claim 1, wherein carbon tetrachloride included in the crude 1,2-dichloroethane fed is recovered in an average concentration of not more than 300 p.p.m. together with 1,2-dichloroethane as a bottom product and the fluctuation range thereof is between 0 and 500 p.p.m.

6. In a method for preparing vinyl chloride which comprises purifying 1,2-dichloroethane by passing through a low boiler column a crude 1,2-dichloroethane produced by oxychlorination of ethylene with at least one of a crude 1,2-dichloroethane produced by direct chlorination of ethylene and a crude uncracked 1,2-dichloroethane recovered in thermal cracking of 1,2-dichloroethane and passing through a high boiler column the bottom product obtained from the low boiler column, and subjecting the purified 1,2-dichloroethane to thermal cracking, the improvement which comprises feeding a crude 1,2-dichloroethane produced by the oxychlorination to an upper plate of a low boiler column, feeding to at least one plate of the low boiler column sufficiently below said upper plate at least one crude 1,2-dichloroethane of a crude 1,2-dichloroethane produced by the direct chlorination and a crude uncracked 1,2-dichloroethane recovered in thermal cracking, and recovering from the low boiler column 1,2-dichloroethane as a bottom product containing 0 to 8,000 p.p.m. of carbon tetrachloride, the concentration of said carbon tetrachloride being stabilized within the fluctuation range of ±500 p.p.m.

7. The method of claim 6, wherein the crude 1,2-dichloroethane fed to the upper plate of the low boiler column further contains as a minor component at least one of crude 1,2-dichloroethane produced by the direct chlorination and a crude uncracked 1,2-dichloroethane recovered in the thermal cracking.

8. The method of claim 6, wherein said at least one crude 1,2-dichloroethane further contains as a minor component a crude 1,2-dichloroethane produced by the oxychlorination.

* * * * *